United States Patent
Behymer et al.

(10) Patent No.: US 9,604,052 B2
(45) Date of Patent: Mar. 28, 2017

(54) MEDICAL DEVICE ANCHORING APPARATUS AND METHODS

(71) Applicant: Medtronic, Inc., Minneapolis, MN (US)

(72) Inventors: Bruce A. Behymer, Grant, MN (US); Eric H. Bonde, Minnetonka, MN (US)

(73) Assignee: Medtronic, Inc., Minneapolis, MN (US)

(*) Notice: Subject to any disclaimer, the term of this patent is extended or adjusted under 35 U.S.C. 154(b) by 542 days.

(21) Appl. No.: 13/795,490

(22) Filed: Mar. 12, 2013

(65) Prior Publication Data
US 2014/0155860 A1 Jun. 5, 2014

Related U.S. Application Data

(60) Provisional application No. 61/733,584, filed on Dec. 5, 2012.

(51) Int. Cl.
*A61B 19/00* (2006.01)
*A61N 1/05* (2006.01)
(Continued)

(52) U.S. Cl.
CPC .......... *A61N 1/0539* (2013.01); *A61M 25/04* (2013.01); *A61B 17/3468* (2013.01);
(Continued)

(58) Field of Classification Search
CPC ..... A61B 19/20; A61B 19/201; A61B 19/203; A61B 2019/208; A61M 25/02; A61M 2025/024; A61M 25/04; A61N 1/0539
See application file for complete search history.

(56) References Cited

U.S. PATENT DOCUMENTS 5,464,446 A 11/1995 Dreessen et al.
5,843,150 A 12/1998 Dreessen et al.
(Continued)

FOREIGN PATENT DOCUMENTS

EP 1016432 A2 7/2000
GB 2344054 A 5/2000
(Continued)

OTHER PUBLICATIONS

Dictionary.com defintion for "press fit" as accessed Mar. 2, 2016; http://dictionary.reference.com/browse/press-fit.*
(Continued)

*Primary Examiner* — Jonathan Miles
(74) *Attorney, Agent, or Firm* — Mueting, Raasch & Genhardt, P.A.

(57) ABSTRACT

Methods and apparatus for anchoring an elongate medical device within a body portal, for example, a stimulation lead in a cranial burr hole, employ opposing engagement surfaces, spring biased toward one another. A retaining member may be inserted between the opposing surfaces, to hold the surfaces apart for initial positioning of the device therebetween. For example, a delivery catheter in which the device is moved through the body portal can serve as the retaining member. In one type of apparatus, the engagement surfaces are formed within an anchoring aperture of one plate member of a pair of plate members. In another type of apparatus, the engagement surfaces are formed by sides of a slot that extend through a ring member and into a plug member, wherein a portion of the plug member is preferably formed by an elastomer material, and, in some cases, an entirety of the apparatus.

8 Claims, 8 Drawing Sheets

(51) Int. Cl.
  *A61M 25/04* (2006.01)
  *A61M 25/02* (2006.01)
  *A61B 17/34* (2006.01)
  *A61N 1/36* (2006.01)
  *A61M 5/00* (2006.01)
  *A61B 90/10* (2016.01)
  *A61B 34/30* (2016.01)
  *A61B 90/11* (2016.01)

(52) U.S. Cl.
  CPC ......... *A61B 17/3472* (2013.01); *A61B 90/11* (2016.02); *A61B 2017/347* (2013.01); *A61B 2034/301* (2016.02); *A61B 2034/302* (2016.02); *A61B 2090/103* (2016.02); *A61M 5/00* (2013.01); *A61M 2025/024* (2013.01); *A61N 1/36025* (2013.01); *A61N 2001/36039* (2013.01)

(56) References Cited

U.S. PATENT DOCUMENTS

| | | | |
|---|---|---|---|
| 5,865,842 A | 2/1999 | Knuth et al. | |
| 5,927,277 A | 7/1999 | Baudino et al. | |
| 5,954,687 A | 9/1999 | Baudino | |
| 6,044,304 A | 3/2000 | Baudino | |
| 6,134,477 A | 10/2000 | Knuteson | |
| 6,210,417 B1 | 4/2001 | Baudino et al. | |
| 6,214,016 B1 | 4/2001 | Williams et al. | |
| 6,321,104 B1 | 11/2001 | Gielen et al. | |
| 6,902,569 B2 | 6/2005 | Parmer et al. | |
| 7,033,326 B1 | 4/2006 | Pianca et al. | |
| 7,177,701 B1 | 2/2007 | Pianca | |
| 7,204,840 B2 | 4/2007 | Skakoon et al. | |
| 7,235,084 B2 | 6/2007 | Skakoon et al. | |
| 7,346,391 B1 | 3/2008 | Osorio et al. | |
| 7,421,297 B2 | 9/2008 | Giftakis et al. | |
| 7,580,756 B2 | 8/2009 | Schulte et al. | |
| 7,588,581 B2 | 9/2009 | Solar et al. | |
| 7,604,644 B2 | 10/2009 | Schulte et al. | |
| 7,604,655 B2 | 10/2009 | Warnick | |
| 7,637,915 B2 | 12/2009 | Parmer et al. | |
| 7,704,260 B2 | 4/2010 | Skakoon et al. | |
| 8,050,772 B1 | 11/2011 | Daglow et al. | |
| 8,738,151 B2 | 5/2014 | Nelson | |
| 2002/0052610 A1 | 5/2002 | Skakoon et al. | |
| 2005/0015128 A1 | 1/2005 | Rezai et al. | |
| 2005/0054985 A1 | 3/2005 | Mogg | |
| 2005/0143800 A1* | 6/2005 | Lando | A61N 1/0539 607/116 |
| 2005/0182420 A1 | 8/2005 | Schulte et al. | |
| 2005/0182421 A1 | 8/2005 | Schulte et al. | |
| 2005/0182422 A1 | 8/2005 | Schulte et al. | |
| 2005/0182423 A1 | 8/2005 | Schulte et al. | |
| 2005/0182424 A1 | 8/2005 | Schulte et al. | |
| 2005/0182425 A1 | 8/2005 | Schulte et al. | |
| 2005/0182464 A1 | 8/2005 | Schulte et al. | |
| 2005/0192594 A1 | 9/2005 | Skakoon et al. | |
| 2007/0233158 A1 | 10/2007 | Rodriguez | |
| 2007/0249980 A1 | 10/2007 | Carrez et al. | |
| 2008/0017206 A1 | 1/2008 | Becker et al. | |
| 2008/0172068 A1 | 7/2008 | Adams et al. | |
| 2009/0088826 A1 | 4/2009 | Bedenbaugh | |
| 2009/0112327 A1 | 4/2009 | Lane et al. | |
| 2009/0118804 A1 | 5/2009 | Moffitt et al. | |
| 2009/0187149 A1 | 7/2009 | Nelson | |
| 2009/0259186 A1 | 10/2009 | Smith et al. | |
| 2010/0023100 A1 | 1/2010 | Barker | |
| 2010/0145357 A1 | 6/2010 | Lane et al. | |
| 2010/0280585 A1 | 11/2010 | Appenrodt et al. | |
| 2011/0238040 A1 | 9/2011 | Johnson et al. | |
| 2012/0010626 A1* | 1/2012 | Daglow | A61N 1/0539 606/129 |
| 2012/0316628 A1 | 12/2012 | Lopez | |
| 2014/0155859 A1 | 6/2014 | Bonde et al. | |
| 2014/0155909 A1 | 6/2014 | Bonde et al. | |

FOREIGN PATENT DOCUMENTS

| | | |
|---|---|---|
| WO | 2005079903 A1 | 9/2005 |
| WO | 20050079903 A2 | 9/2005 |
| WO | 2008054691 A2 | 5/2008 |
| WO | 2009055746 A2 | 4/2009 |
| WO | 20090055746 A2 | 4/2009 |
| WO | WO 2014089360 A2 | 12/2014 |
| WO | WO 2014089366 A2 | 12/2014 |
| WO | WO 2014089371 A2 | 12/2014 |

OTHER PUBLICATIONS

U.S. Appl. No. 13/795,441; Office Action issued Jan. 29, 2015.
PCT Patent Application No. PCT/US2013/073419, filed Dec. 5, 2013; International Preliminary Report on Patentability issued Jun. 18, 2015; 12 pages.
PCT Patent Application No. PCT/US2013/073429, filed Dec. 5, 2013; International Preliminary Report on Patentability issued Jun. 18, 2015; 13 pages.
PCT Patent Application No. PCT/US2013/073436, filed Dec. 5, 2013; International Search Report and Written Opinion issued Aug. 28, 2014; 16 pages.
PCT Patent Application No. PCT/US2013/073436, filed Dec. 5, 2013; International Preliminary Report on Patentability issued Jun. 18, 2015; 10 pages.
U.S. Appl. No. 13/795,441; Office Action issued May 26, 2015; 10 pages.
U.S. Appl. No. 13/795,458; Office Action issued May 7, 2015; 13 pages.
International Search Report and The Written Opinion, PCT/US2013/073429, Jul. 24, 2014, 19 pages.
The International Search Report and The Written Opinion, PCT/US2013/073419, Jul. 2, 2014, 19 pages.
Invitation to Pay Additional Fees and Communication Relating to the Result of the Partial International Seach, PCT/US2013/073436, Apr. 10, 2014, 6 pages.
Invitation to Pay Additional Fees, PCT/US2013/073429, Feb. 27, 2014, 5pps.
Guardian Cranial Burr Hole Cover System, Clinician's Manual, ANS, Apr. 2009.
PCT Patent Application No. PCT/US2013/073419, filed Dec. 5, 2013; Invitation to Pay Additional Fees and Communication Relating to the Results of the Partial International Search issued Apr. 9, 2014, 7 pages.
U.S. Appl. No. 13/795,441; Office Action issued Oct. 2, 2015.
U.S. Appl. No. 13/795,441; Office Action issued Dec. 9, 2015.
U.S. Appl. No. 13/795,458; Office Action issued Oct. 8, 2015.
U.S. Appl. No. 13/795,441, filed Mar. 12, 2013, Bonde et al.
U.S. Appl. No. 13/795,458, filed Mar. 12, 2013, Bonde et al.
U.S. Appl. No. 13/795,441; Advisory Action issued Feb. 19, 2016; 3 pages.
U.S. Appl. No. 13/795,458; Advisory Action issued Dec. 17, 2015; 3 pages.

* cited by examiner

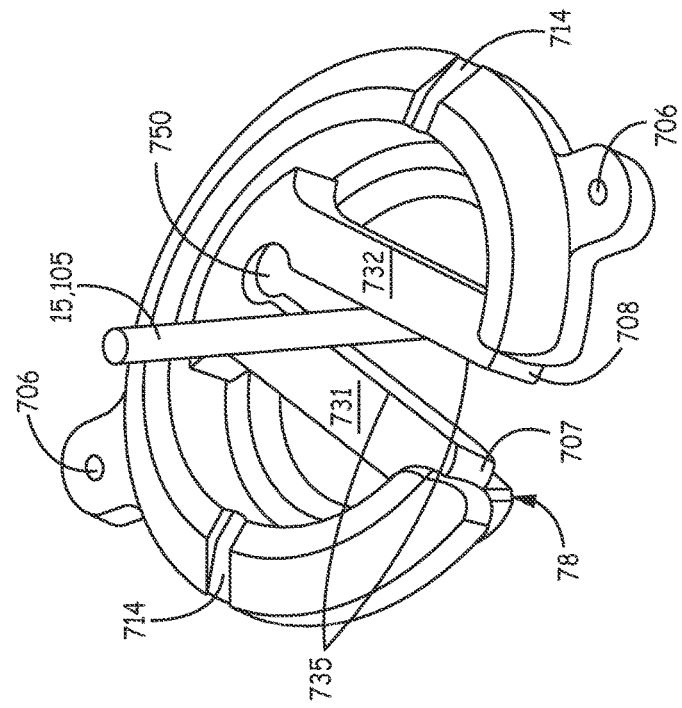
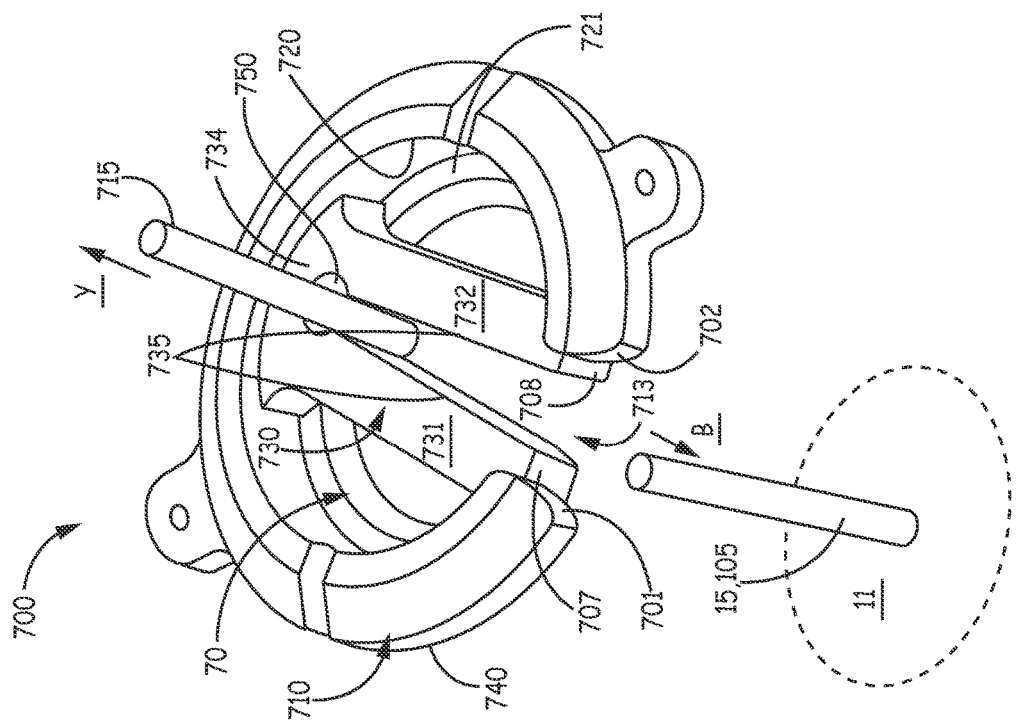

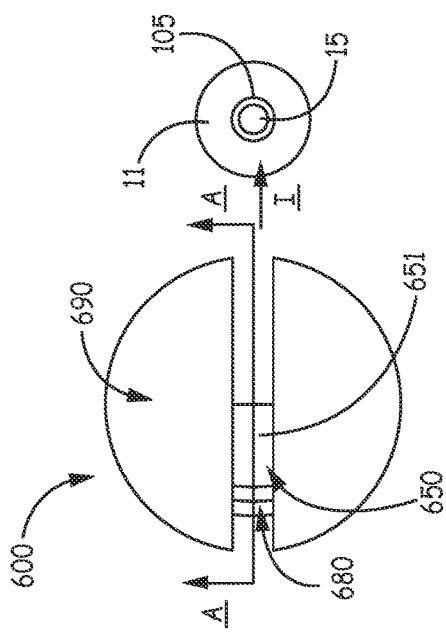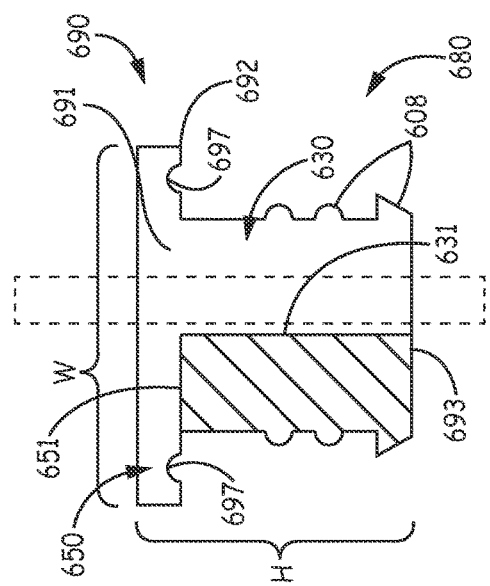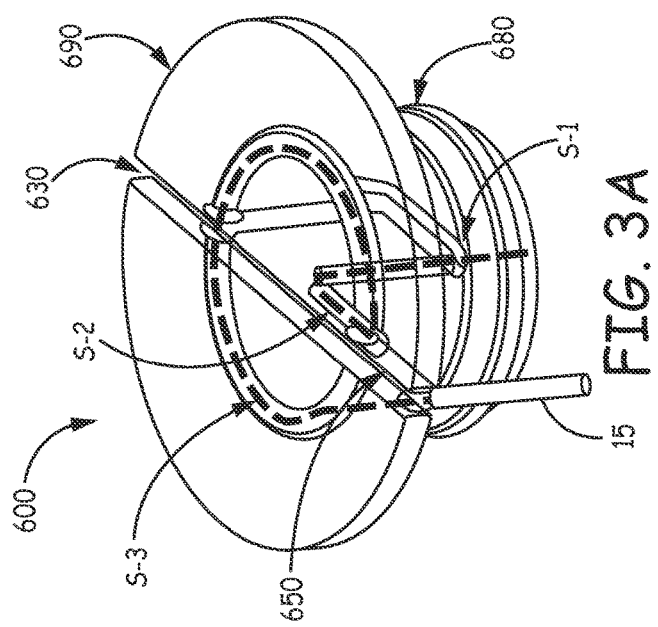

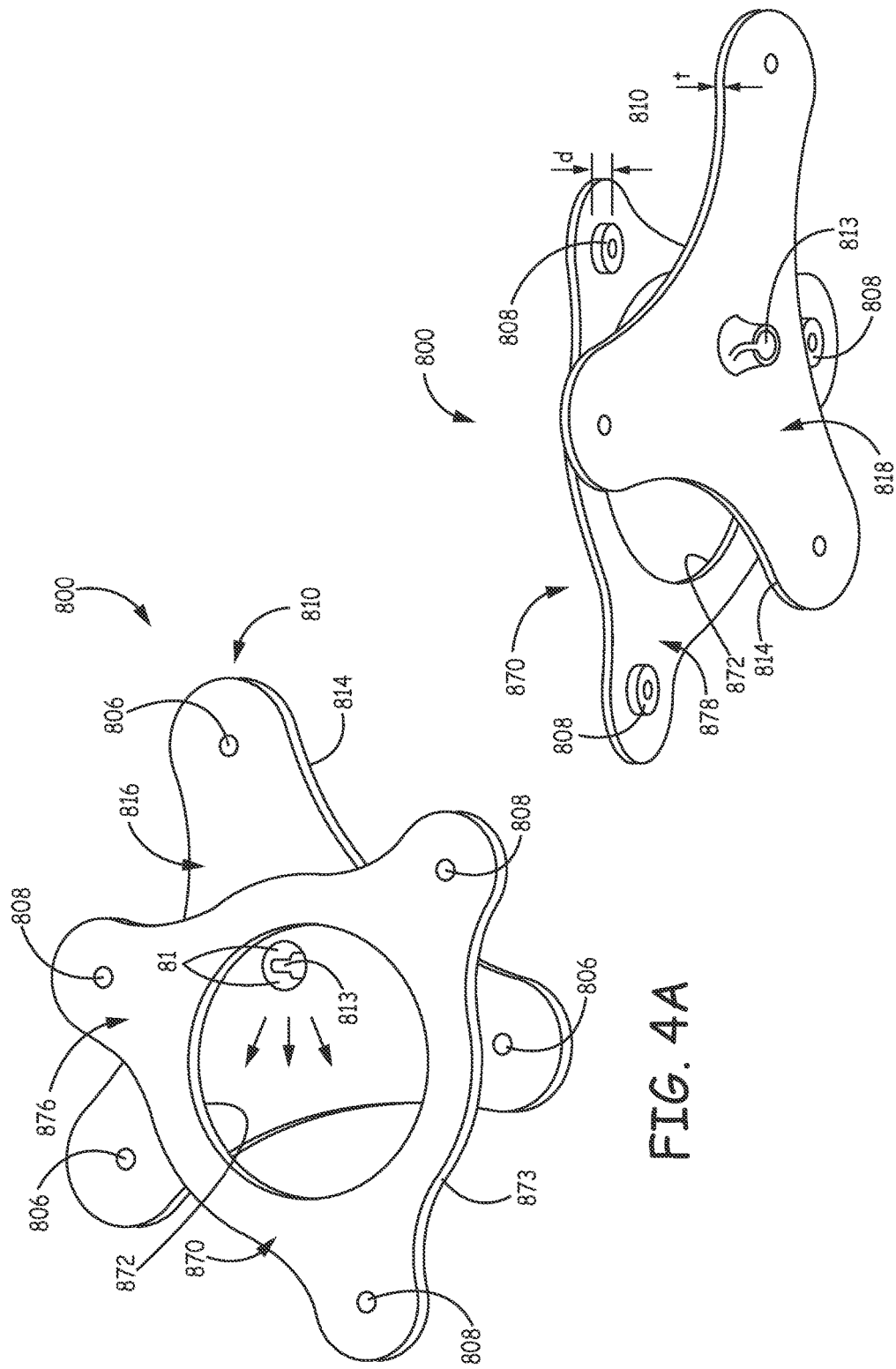

MEDICAL DEVICE ANCHORING APPARATUS AND METHODS

CROSS-REFERENCE TO RELATED APPLICATION(S)

The present application claims priority to U.S. Provisional Patent Application Ser. No. 61/733,584, which was filed on Dec. 5, 2012, and is hereby incorporated by reference in its entirety. The present application is related to the following commonly assigned and co-pending United States Non-provisional Patent Applications, filed concurrently herewith and having the same title as the instant application, each of which is hereby incorporated by reference in its entirety: application Ser. No. 13/795,441, and application Ser. No. 13/795,458.

TECHNICAL FIELD

The present disclosure pertains to medical devices and more particularly to various apparatus, assemblies and methods for anchoring an elongate medical device within a body portal, for example, a burr hole formed in a skull of a patient.

BACKGROUND

Medical procedures for treating a variety of neurological conditions, for example, Parkinson's disease, essential tremor and dystonia, require access to the brain, typically through a burr hole formed in the skull, for the insertion of deep brain stimulating electrodes. Burr holes may also be formed for the insertion of a delivery catheter, for example, to provide drug therapy for similar conditions. Stereotactic apparatus and procedures, which are known to those skilled in the art, may be employed by surgeons to locate inserted electrodes and/or drug delivery ports in target regions of the brain.

FIG. 1A is a perspective view of an exemplary stereotactic guidance system 100 (e.g. Medtronic Nexdrive Micropositioning Drive attached to the Medtronic Nexframe®) mounted to a patient's skull. FIG. 1A illustrates a ring 120 of guidance system 100, which extends around a perimeter of a burr hole 11 formed in the skull, supporting a socket assembly 140 to which a micropositioning drive 160 is attached. Burr hole 11 may be lined with a base ring 112 (FIG. 1B; e.g. the Medtronic Stimloc base) that is mounted around burr hole 11 prior to attaching ring 120 of guidance system 100. FIG. 1 further illustrates an elongate medical device 15, for example, a medical electrical lead carrying one or more stimulating electrodes, held within drive 160 for advancement through burr hole 11 and into the target region of the brain.

FIG. 1B illustrates a portion of the implanted device 15, after guidance system 100 is removed, extending proximally out from base ring 112, which lines burr hole 11, and which is fastened to the skull, for example, via screws received through holes 106 in base ring 112. Those skilled in the art appreciate that a proximal portion of implanted device 15, outside the cranial space, may be routed, beneath the scalp and subcutaneously, to a therapy generator (not shown), for example, implanted in proximity to the clavicle. FIG. 1B further illustrates device 15 extending through a slot of base ring 112 so that device 15 may be secured/anchored between base ring 112 and a cap that snaps into place thereover (not shown; e.g., the Medtronic Stimloc cap). Although various configurations of apparatus for securing elongate medical devices in body portals, such as burr holes, are known in the art, there is still a need for new and improved anchoring apparatus and methods, for example, to increase the ease by which anchoring is activated, without dislodging the implanted device, and without compromising the stability of anchoring.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 2A-B are perspective views of an anchoring apparatus, according to some embodiments;

FIG. 3A is a perspective view (partially transparent) of an anchoring apparatus, according to some embodiments;

FIGS. 3B-C are a top plan view and a cross-section view of the apparatus shown in FIG. 3A;

FIGS. 4A-B are perspective views of an anchoring assembly, according to yet further embodiments;

DETAILED DESCRIPTION

Embodiments of anchoring apparatus and assemblies, disclosed herein, are suitable for mounting/fixing in or over a body portal, for example, a cranial burr hole, in order to anchor in place an implanted elongate medical device, such as an electrical lead or a fluid delivery catheter, which is implanted in the body via insertion through the body portal. The apparatus and assemblies include various configurations of spring biased engagement surfaces, which may be retained in an open position while the elongate medical device is positioned therebetween, either before or after the apparatus/assembly is fixed relative to the body portal. Associated methods for employing the various apparatus and assemblies are disclosed in conjunction with the detailed description of each exemplary embodiment thereof, and in summary at the end of the detailed description. The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 2C:
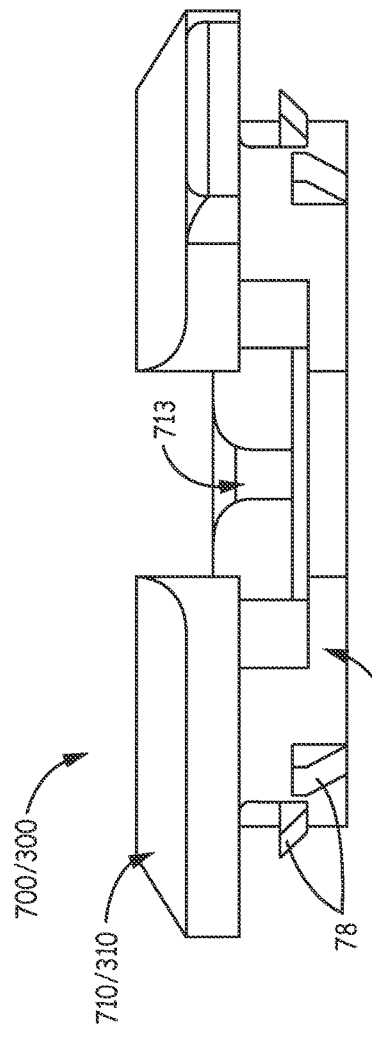
FIG. 2C is an elevation view of an anchoring apparatus, according to some embodiments.

FIGS. 2A-B are perspective views of an anchoring apparatus 700, according to some embodiments. FIGS. 2A-C illustrate apparatus 700 including a central, or plug portion 70 and ring member 710, which extends around a perimeter of plug portion 70; a slot 713 extends from an opening thereof, formed through ring member 710, between outer and inner perimeter surfaces 740, 720 thereof, and into plug portion 70. FIGS. 2A-B further illustrate plug portion 70 including spring biased opposing engagement surfaces 735 that form opposing sides of slot 713, wherein opposing sides of slot 713 are defined by opposing arms 731, 732 of a spring member 730 of plug portion 70. Spring member 730 is shown including a fixed end 734, which is coupled to inner perimeter surface 720 of ring member 710, and from which each of a pair of opposing arms 731, 732 extends to a corresponding moveable end 707, 708 thereof.

With further reference to FIGS. 2A-B, each of first and second moveable ends 707, 708 are contained within inner perimeter surface 720 of ring member 710 such that ends 707, 708 are slideable therealong, to be opened, away from one another, against the spring bias thereof, as shown in FIG. 2A, and then allowed to close toward one another, according to the spring bias thereof, as shown in FIG. 2B. Plug portion 70 is shown including an optional ledge 721 that extends around inner perimeter surface 720 of ring member 710; if included, ledge 721 preferably extends in proximity to each end 701, 702 of ring member 710, at the opening of slot 713, to support ends 707, 708 of spring member 730. It should be noted that, if included, ledge 721 may only extend in proximity to each end 701, 702. According to some embodiments, anchoring apparatus 700 further includes a retaining member, for example, a pin-like tool 715, which is shown inserted between arms 731, 732 of spring member 730 in FIG. 2A, for example, within a base hole 750 of spring member 730, to hold arms 731, 732 of spring member 730 apart, so that an elongate medical device, for example, lead 15, which is shown extending out from burr hole 11, may be inserted into the opening of slot 713 and in between opposing engagement surfaces 735, for example, by moving apparatus 700 per arrow B.

Figures 1A, 1B:
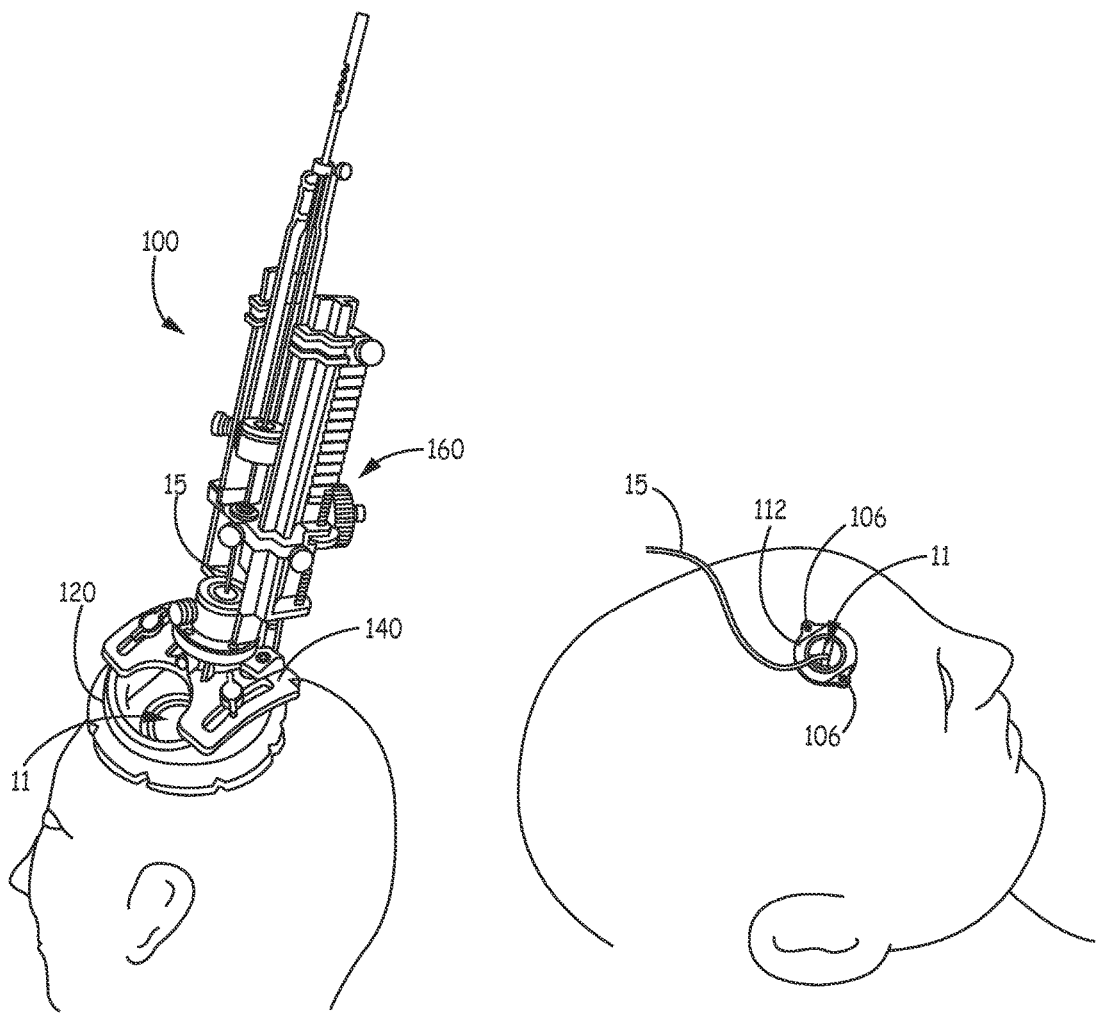
FIG. 1A is a perspective view of an exemplary stereotactic guidance mounted to a patient's skull.
FIG. 1B shows an exemplary base ring mounted in a burr hole of the skull.

According to some methods, after lead 15 is implanted through the body portal/burr hole 11, for example, via the above described guidance system 100 (FIG. 1A), lead 15 is positioned between engagement surfaces 735, and then, with reference to the elevation view of FIG. 2C, an outer perimeter surface of plug portion 70, which extends below ring 710, and which is defined by press fit features 78, is press fit within burr hole 11. Subsequently, retaining member/tool 715 may be removed, per arrow Y, to allow arms 731, 732 of spring member 730 to move together according to the spring bias thereof, thereby anchoring lead 15 between engagement surfaces 735, as illustrated in FIG. 2B. Once anchored, a proximal portion of lead 15 may be received in one of channels 714, which are formed in ring member 710, and may guide routing of the proximal end of lead 15 to another site in the body for connection to a therapy generator. FIGS. 2A-B further illustrate outer perimeter surface 740 of ring member 710 having fastening features extending therefrom, wherein the fastening features include holes 706 through which screws may be inserted for fastening the press fit anchoring apparatus 700 to the skull surrounding burr hole 11, for example, prior to removing the retaining member to anchor lead 15.

According to some alternate methods, apparatus 700 may be positioned around a delivery catheter 105, which extends from the body portal/burr hole 11, after which plug portion 70 may be press fit within hole 11, and retaining member/tool 715 removed to temporarily hold catheter 105 in place while a device, such as lead 15, is delivered therethrough for implant. Then, once lead 15 is implanted, catheter 105 is withdrawn, over lead 15, out from hole 11, and from between arms 731, 732, to allow engagement surfaces 735 to move together, according to the spring bias of arms 731, 732, and, thereby anchor lead 15.

A distance between arms 731, 732 in a spring biased closed position, without lead 15 or any retaining member positioned therebetween, is preferably less than a diameter of lead 15, for example, a distance of approximately 0.040 inch when the lead diameter is approximately 0.055 inch; this interference condition combined with the material properties of spring member 730 defines a holding force. Spring member 730 may be integrally formed with ring member 210, for example, by injection molding, from a biocompatible polymer material, such as polyurethane, polycarbonate, polysulfone, polyether ether ketone (PEEK), or nylon. Alternately, spring member 730 is formed as a separate part, wherein end 734 is subsequently attached to ring member 710 along inner perimeter surface 720, as shown. According to an exemplary embodiment, spring member 730 is formed from a relatively high durometer polyurethane, and ring member 710 from a relatively low durometer polyurethane, and then member 730 and ring 710 are ultrasonically welded, or solvent bonded together. According to some alternate embodiments, spring member 730 may be formed by overmolding a metal core, for example, a stainless steel alloy or nitinol torsional spring, with a biocompatible polymer such as polyurethane.

Figure 2E:
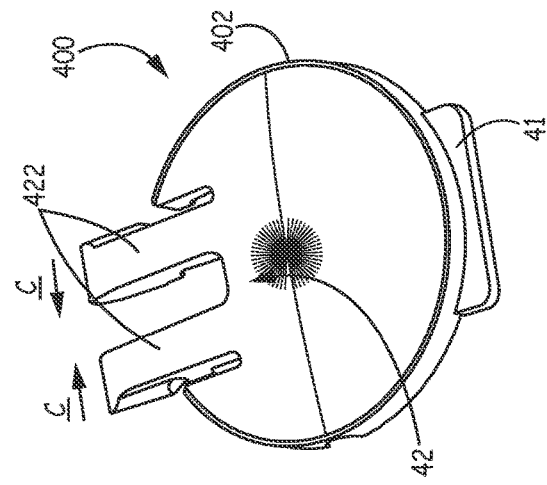
FIG. 2E is a perspective view of a cap, which may be employed with the apparatus of FIG. 2D, according to some embodiments.
Figure 2D:
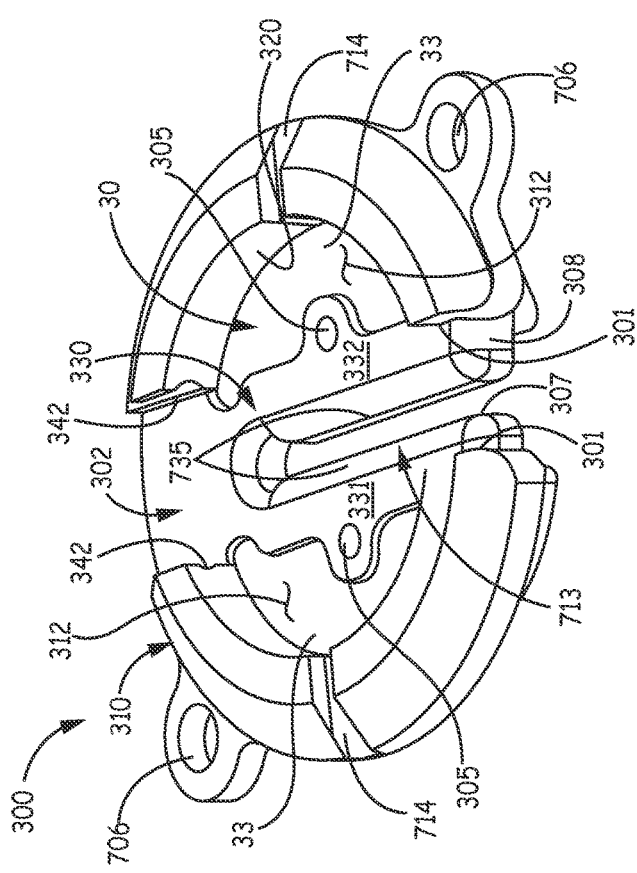
FIG. 2D is a perspective view of an anchoring apparatus, modified from that shown in FIGS. 2A-B, according to some embodiments.

FIG. 2D is a perspective view of an anchoring apparatus 300, modified from that shown in FIGS. 2A-B, according to some embodiments. FIG. 2D illustrates apparatus 300 including a central, or plug portion 30 and a ring member 310, which extends around a perimeter of plug portion 30; like apparatus 700, apparatus 300 has slot 713 extending from an opening thereof, formed through ring member 310, and into plug portion 30. FIG. 2D further illustrates plug portion 30 including spring biased opposing engagement surfaces 735 that form opposing sides of slot 713, wherein opposing sides of slot 713 are defined by opposing arms 331, 332 of a spring member 330 of plug portion 30. Spring member 330 is similar to spring member 730 of apparatus 700 in that spring member 330 includes a pair of opposing arms 331, 332, wherein each arm 331, 332 extends between a fixed end 334 of spring member 330, which is coupled to ring member 310, and a corresponding moveable end 307, 308; but plug portion 30 of apparatus 300 further includes an elastomer material 33, for example, a medical grade silicone rubber, that extends between each arm 331, 332 and an inner perimeter surface 320 of ring member 310, on either side of slot 713, and is compressed when arms are forced apart, for example, by the above-described retaining member. The inclusion of elastomer material 33 enhances the spring bias provided by arms 331, 332 to opposing engagement surfaces 735, and may further enhance sealing of burr hole, when apparatus 700 is press fit therein. Furthermore, with reference to the elevation view of FIG. 2C, all or a portion of press fit features 78 may be formed by an extent of elastomer material 33.

A distance between arms 331, 332 in a spring biased closed position, like arms 731, 732 of apparatus 700, is preferably less than a diameter of the medical device to be anchored between engagement surfaces 735, for example, a distance of approximately 0.040 inch, when a device diameter is approximately 0.055 inch. Spring member 330 may be integrally formed with ring member 310, for example, by injection molding, from a biocompatible polymer material, such as polyurethane, polycarbonate, polysulfone, polyether ether ketone (PEEK), or nylon. Alternately, spring member 330 is formed as a separate part, wherein end 334 is subsequently attached to ring member 310. According to an exemplary embodiment, spring member 330 is formed from a relatively high durometer polyurethane, and ring member 310 from a relatively low durometer polyurethane, and then member 330 and ring 310 are ultrasonically welded, or solvent bonded together.

Methods described above for anchoring an elongate medical device within a body portal, for example, lead 15 in burr hole 11, are generally applicable to anchoring apparatus 300. But, according to alternative methods, another type of retaining member may be employed with apparatus 300. With further reference to FIG. 2D, each arm 331, 332 of spring member 330 includes an aperture 305 to mate with a retaining member, for example, a forceps-type tool used to spread arms 331, 332 apart from one another, while the elongate medical device and/or catheter is inserted between engagement surfaces 735. With further reference to FIG. 2D, in conjunction with FIG. 2E, following routing of the proximal portion of the anchored implanted device, for example, being guided by receipt thereof in one of channels 714, a cap 400 is preferably secured in place over plug portion 30.

FIG. 2D illustrates ring member 310 protruding from an upper surface 312 of plug portion 30, and including a mounting groove 302 and opposing edges 301, which are located on either side of the opening of slot 713, and which overhang moveable ends 307, 308 of arms 331, 332. With reference to FIG. 2E, edges 301 and mounting groove 302 provide mating features for cap 400 to cover upper surface 312 of plug portion 30, when an outer perimeter edge 402 of cap 400 is contained within an inner perimeter surface 320 of ring member 310. According to the illustrated embodiment, a first perimeter tab 41 of cap 400 may be inserted beneath the overhang of opposing edges 301 of ring member 310, and a second compressible tab 42 may be compressed, per arrows C, to fit tab 42 within mounting groove 302 of ring member 310. FIG. 2E illustrates tab 42 being formed by opposing resilient prongs, each of which includes a protruding feature 422, which is configured to interlock with a corresponding sidewall 342 of mounting channel 302 of ring member 310, according to some embodiments.

FIG. 3A is a perspective view (partially transparent) of an anchoring apparatus 600, FIG. 3B is a top plan view of apparatus 600, and FIG. 3C is a cross-section view through section line A-A of FIG. 3B, according to some embodiments. FIGS. 3A-C illustrate apparatus 600 including a plug portion 680 and a ring member 690, which extends around a perimeter of plug portion 680, wherein plug portion 680 and ring member 690 are preferably integrally formed, for example, from molded medical grade silicone rubber. FIGS. 3A-C further illustrate plug portion 680 including a top section 691, of which ring member 690 is an outward extension, and a bottom surface 693, wherein a first slot 630 extends, between top section 691 and bottom surface 693, from a longitudinally extending opening (spanning a height H of apparatus 600), at an outer perimeter surface of both plug portion 680 and ring member 690, to a longitudinally extending end wall 631, within plug portion 680. Another, second slot 650 is shown communicating with first slot 630 (best seen in cross-section A-A of FIG. 3C), wherein second slot 650 extends from an opening at top section 691 (spanning a width W of apparatus 600) to a radially extending end wall 651, within plug portion 680. FIG. 3C further illustrates an optional channel 697 formed in a lower surface 692 of ring member 690 that projects radially outward from plug 680.

With further reference to FIG. 3B, a body portal, for example, burr hole 11 formed in a skull of a patient, is schematically represented in proximity to anchoring apparatus 600. FIG. 3B illustrates delivery catheter 105 inserted through hole 11 to guide a lead 15, which is contained therein, to a target region of the patient's brain. According to the illustrated embodiment, apparatus 600 may be positioned around catheter 105 and lead 15, per arrow I, such that catheter 105 (shown with dashed lines in FIG. 3C) extends in proximity to end wall 631 of first slot 630, after which, plug portion 680 may be press fit into hole 11. FIG. 3B further illustrates an outer perimeter surface of plug portion 680 being defined by press fit features 608, which facilitate insertion into hole 11 and subsequent stability of plug 680 within hole 11. Following the press fit of plug 680, a distal end of lead 15 may be passed through catheter 105 and implanted in the target region of the brain, and then catheter 105 withdrawn out from hole 11 and apparatus 600, and over lead 15, to leave a segment of the implanted lead 15 captured within slot 630. A more proximal portion of lead 15, which extends outside apparatus 600, may anchor lead within apparatus 600 according to the bold dashed line of FIG. 3A. With reference to FIG. 3A, in conjunction with FIGS. 3B-C, the segment of lead 15 that extends alongside inner end wall 631 of first slot 630 is designated as a first segment S-1; a more proximal segment of lead 15, adjacent to first segment S-1, is designated as a second segment S-2, and is shown extending alongside adjacent inner end wall 651 of second slot 650; and a more proximal segment, adjacent to second segment S-2, is designated as a third segment S-3, and is shown extending around plug 680 in proximity to lower surface 692 of ring member 690, for example, being routed along the aforementioned optional channel 697. Thus, lead 15 is anchored with apparatus 600, after inserting first segment S-1 of lead 15 into first slot 630, by bending second segment S-2 into second slot 650, and then wrapping third segment S-3 around plug 680, adjacent to, and beneath the radial projection of ring member 690.

Figure 3D:
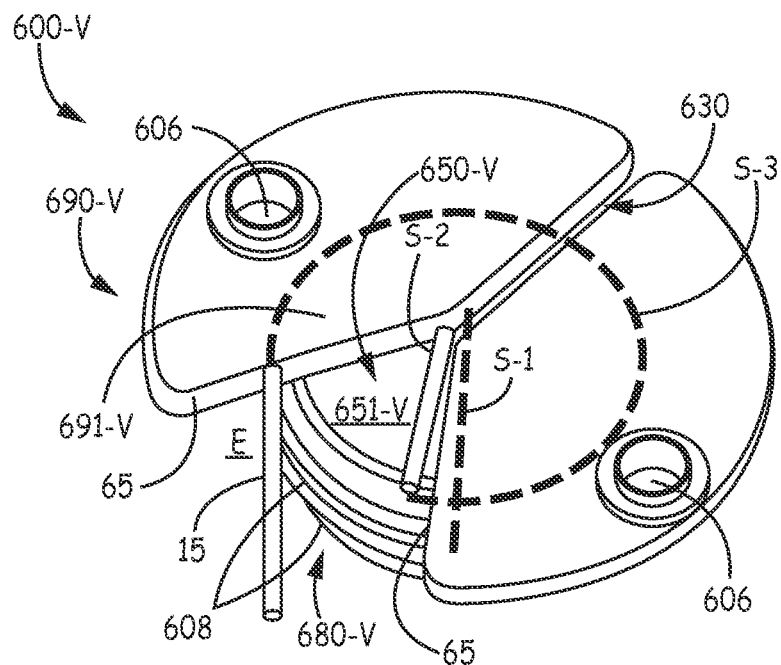
FIG. 3D is a perspective view of an anchoring apparatus, according to some alternate embodiments.
Figure 3E:
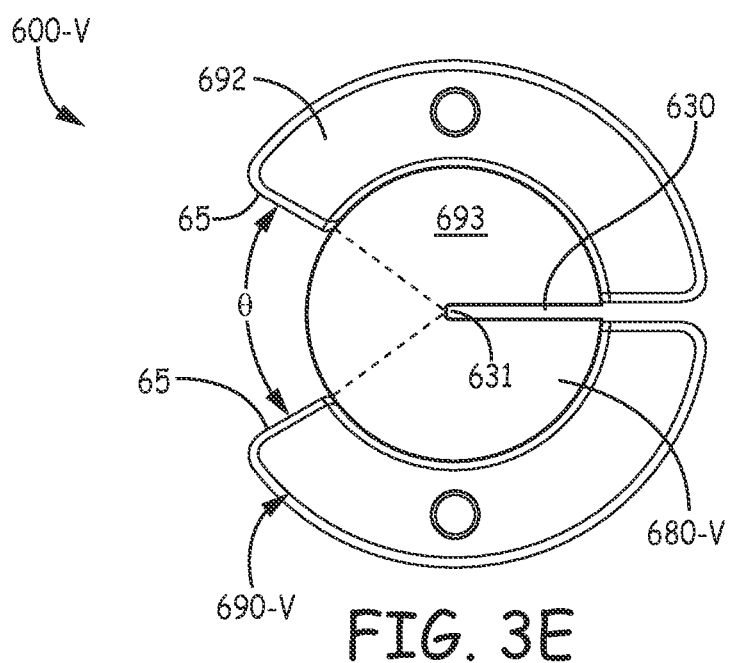
FIG. 3E is a bottom plan view of the anchoring apparatus shown in FIG. 3D, according to some embodiments.

FIG. 3D is a perspective view of an anchoring apparatus 600-V, which is similar to apparatus 600, described above. FIG. 3D illustrates apparatus 600-V including a plug portion 680-V and a ring member 690-V, which are preferably integrally formed, for example, from a molded medical grade silicone rubber, and wherein ring member 690-V is an outward extension of a top section 691-V of plug portion 680-V. Apparatus 600-V, like apparatus 600, has first slot 630 extending from an opening, at the outer perimeter surfaces of ring member 690-V and plug portion 680-V, to longitudinally extending end wall 630 within ring member 690-V and plug portion 680-V, as best seen in the bottom plan view of FIG. 3E; wherein first slot 630 communicates with a second slot 650-V, which extends from an opening at top section 691-V to a radially extending end wall 651-V within plug portion 680-V. Apparatus 600-V differs from apparatus 600 in that opposing sides 65 of second slot 650-V open out from one another, for example, to enclose an angle θ (FIG. 3E), which is between approximately ten degrees and approximately ninety degrees.

With further reference to FIG. 3D, it may be appreciated that lead 15 may be anchored in apparatus 600-V, via segments S-1, S-2 and S-3 thereof, in a similar manner to that described for apparatus 600, but that outward opening sides 65 of second slot 650-V help to reduce a profile of apparatus 600-V and lead 15, anchored therein, in the area where lead 15 exits apparatus 600-V, which area is designated with reference letter E. FIG. 3D illustrates apparatus 600-V including press fit features 608 formed along the outer perimeter surface of plug portion 680-V, similar to plug portion 680, and apparatus 600-V further including fastening features in the form of reinforced holes 606 that are formed through ring member 690-V. According to the illustrated embodiment, holes 606 are configured to receive screws for fastening anchoring apparatus 600-V to the skull surrounding burr hole 11, after plug portion 680-V of apparatus 600-V has been press fit within burr hole 11. Such holes 606 may also be included in apparatus 600 of FIGS. 3A-C, according to some embodiments.

Figure 4C:
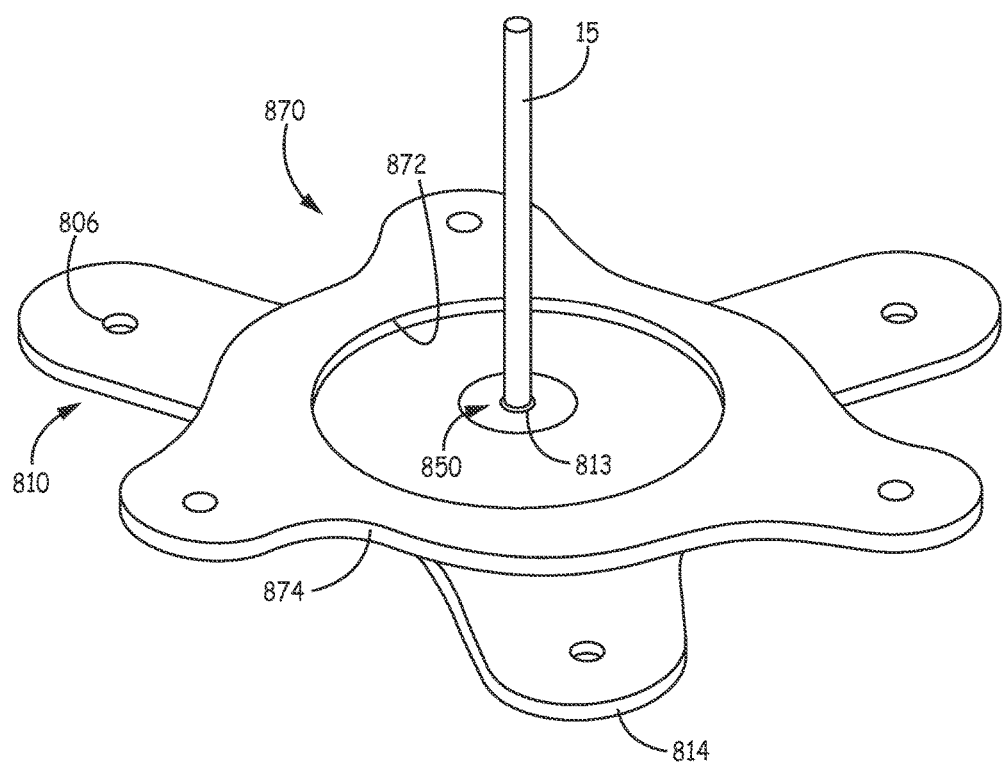
FIG. 4C is a perspective view of an anchoring apparatus, modified from that shown in FIGS. 4A-B, according to some embodiments.

FIGS. 4A-C are perspective views of an anchoring assembly 800, according to yet further embodiments, wherein embodiments of opposing engagement surfaces are formed in an aperture 813 of a plate member 810. FIGS. 4A-B illustrate assembly 800 including a pair of relatively thin plate members 870, 810 positioned adjacent one another so that a second side 878 of first plate member 870 faces a first side 816 of second plate member 810. Plate members 870, 810 may be formed from titanium or a stainless steel alloy. A nominal thickness of each plate member 870, 810 may be approximately 1 mm, and the extent of each plate member 870, 810 is, preferably, slightly curved, according to some embodiments, for example, to conform to a contour of a skull when secured thereto, as will be described in greater detail below.

FIGS. 4A-B further illustrate an inner perimeter edge 872 of first plate member 870 defining an opening that extends therethrough, from a first side 876 to second side 878, and securing/fastening features 808 of first plate member 870 located in proximity to an outer perimeter edge 874 thereof. Each securing feature 808 is shown including a hole through which a screw/bone fastener may be inserted to secure first plate member 870 over a body portal; and each securing feature 808 is shown projecting from second side 878 of plate member 870 by a distance d. According to the illustrated embodiment, a nominal thickness t of second plate member 810 is less than or approximately equal to distance d so that, when first plate member 870 is secured to a surface surrounding the body portal, for example, burr hole 11, second plate member 810 may fit within the "standoff" between first plate member 870 and the surface.

FIGS. 4A-B further illustrate second plate member 810 including an anchoring aperture 813 that is formed therethrough, from first side 816 to a second side 818 thereof, wherein aperture 813 has opposing engagement surfaces 81 spring biased toward one another to give aperture 813 a relaxed diameter that is less than an outer diameter of a device to be anchored therein, for example, lead 15 (FIG. 4C). Engagement surfaces 81, may be force to expand from the relaxed diameter, for passage of the device therethrough, for example, via insertion of a delivery catheter through aperture 813, wherein the delivery catheter has a lumen to receive passage of the device therethrough. Once the catheter is removed from around the device, engagement surfaces 81 move back toward one another, according to the spring bias, to anchor the device in aperture 813. According to FIGS. 4A-B, aperture 813 is integrally formed in plate member 810 as a dimple spring clip, but, according to an alternate embodiment shown in FIG. 4C, opposing engagement surfaces of anchoring aperture 813 are formed by an elastomer insert 850, for example, a silicone grommet.

With further reference to FIGS. 4A-B, second plate member 810 has a shape, defined by an outer perimeter edge 814 thereof, which, in addition to the aforementioned thickness of second plate member 810, allows second plate member 810 to be captured between secured first plate member 870 and the body portal, such that anchoring aperture 813 is located within a boundary of the opening defined by inner perimeter edge 872, while each securing feature 806 of second plate member 810 is located outside a boundary defined by outer perimeter edge 873 of first plate member 870. Furthermore, the aforementioned standoff provided by the projection of securing features 808 of first plate member 870 allows the captured second plate member 810 to be moved, for example, according to any of the bold arrows shown in FIG. 4A, to reposition anchoring aperture 813 over the body portal and within the boundary defined by inner perimeter edge 871, prior to securing second plate member 810, for example, via screws inserted through holes/securing features 806, to the surface surrounding body portal.

Figure 5:
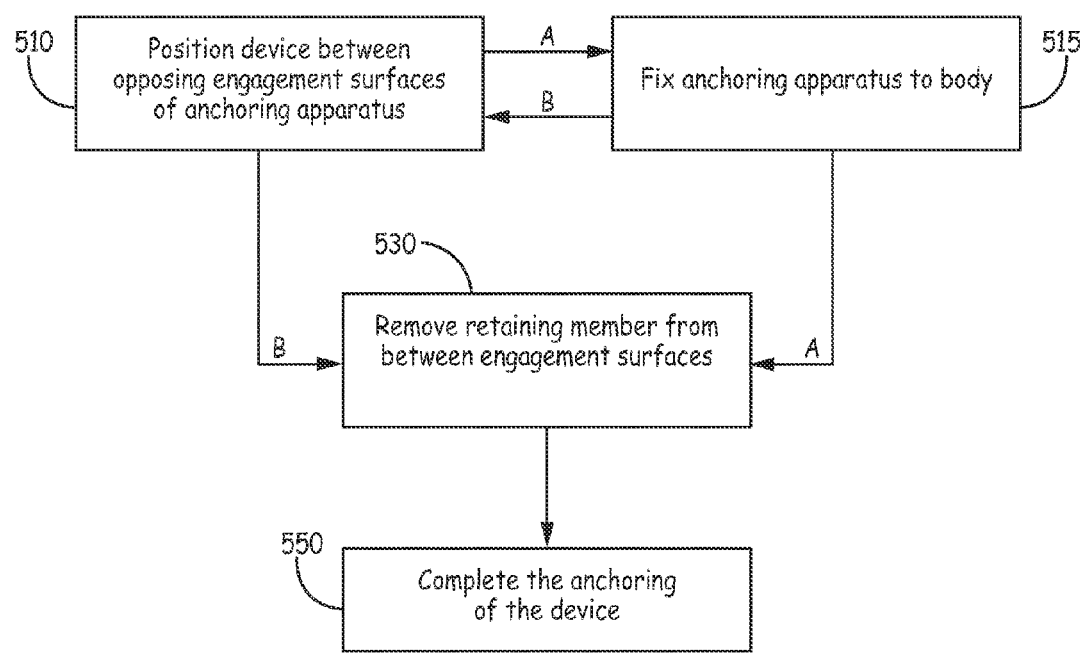
FIG. 5 is a flow chart outlining some methods of the present invention.

FIG. 5 is a flow chart outlining some methods of the present invention, for example, that employ any of the above-described embodiments of anchoring apparatus and assemblies. According to some methods, an elongate medical device, for example, the above described lead 15, may be inserted between opposing engagement surfaces of an anchoring apparatus, per step 510, after the device has been positioned at a target location in a body, via passage through a body portal, if the anchoring apparatus includes engagement surfaces formed by opposing sides of a slot, like those embodiments described above in conjunction with FIGS. 2A-3E. Following step 510, per path A, the anchoring apparatus is fixed to the body, for example the skull surrounding cranial burr hole 11, per step 515, and then a retaining member, which has held the opposing engagement surfaces apart from one another, against a spring bias thereof, is removed from between the engagement surfaces of the apparatus, per step 530, so that the spring bias moves the engagement surfaces toward one another and into contact with the inserted device. The retaining member may be a separate tool, which extends between the engagement surfaces alongside the inserted device, for example, tool 715 of FIG. 2A, or a delivery catheter within which the device is received for positioning at the target location, for example, catheter 105 of FIG. 3B. According to some alternate methods, the anchoring apparatus is fixed to the body, per step 515, and then, following path B, the device is positioned between the opposing engagement surfaces thereof, which are held apart by the retaining member, per step 510. The embodiments according to FIGS. 4A-C, which include an anchoring aperture, are suited for the alternate path B, wherein first plate member 870 is secured to the body to capture second plate member 810 over the body portal, after which a delivery catheter, as the retaining member, is inserted through anchoring aperture 813 of second plate member 810, so that the device may be positioned between the engagement surfaces of anchoring aperture 813 via passage through the inserted catheter. It should be noted that a position of the captured second plate member 810 over the body portal may be adjusted during the insertion of the catheter and the passage of the device through the catheter, before securing second plate member 810 to the body and moving on to step 530. It should also be noted that slotted embodiments of FIGS. 2A-3E may be employed per path B as well. With further reference to FIG. 5, in step 550, the anchoring of device is completed, for example, by routing a proximal segment of the device into a channel, or another slot, of the anchoring apparatus. In some cases, following routing, a cap is secured over the anchoring apparatus.

In the foregoing detailed description, the invention has been described with reference to specific embodiments and methods. However, it may be appreciated that various modifications and changes can be made without departing from the scope of the invention as set forth in the appended claims.

The invention claimed is:

1. An anchoring apparatus for an elongate medical device, the apparatus comprising:
   a plug portion including opposing engagement surfaces and a press fit feature defining an outer perimeter surface of the plug portion, the engagement surfaces being spring biased toward one another to anchor the medical device therebetween, wherein the plug portion further comprises a spring member creating the spring bias for the engagement surfaces, the spring member including a fixed end and a pair of opposing arms, each arm extending from the fixed end to a corresponding moveable end thereof;
   a ring member extending around a perimeter of the plug portion, above the press fit feature, the ring member including at least one channel to receive a segment of the device when the device is anchored between the engagement surfaces, wherein a slot extends from a slot opening formed through the ring member and into the plug portion, the engagement surfaces of the plug portion being formed by opposing sides of the slot, and wherein the ring member further includes: opposing edges located on either side of the slot opening; and a mounting groove extending through the ring member opposite the slot opening, wherein each of the opposing edges overhangs the moveable end of the corresponding arm of the spring member; and
   a cap configured to cover the plug portion when fitted within the ring member, the cap including a first perimeter tab and a second, compressible perimeter tab, opposite the first perimeter tab, wherein when the cap is fitted within the ring member to cover the plug portion, the first perimeter tab is located beneath the overhang of the opposing edges of the ring member, and the second compressible perimeter tab is held within the mounting groove of the ring member.

2. The anchoring apparatus of claim 1, wherein the opposing arms of the spring member define the opposing sides of the slot.

3. The anchoring apparatus of claim 1, wherein the plug portion further includes an elastomer material, which extends between each arm of the spring member and an inner perimeter surface of the ring member on either side of the slot.

4. The apparatus of claim 1, wherein the movable ends of the arms of the spring member are supported by an inner perimeter surface of the ring member.

5. The apparatus of claim 1, further comprising a retaining member, the retaining member being configured to engage with, and disengage from the spring member, between the arms thereof, the engaged retaining member holding the engagement surfaces apart from one another against the spring bias, and the disengaged retaining member allowing the engagement surfaces to move toward one another according to the spring bias.

6. The apparatus of claim 1, wherein the ring member protrudes from an upper surface of the plug portion.

7. The apparatus of claim 1, wherein the plug portion and ring member are wholly and integrally formed from an elastomer material.

8. An anchoring apparatus for an elongate medical device, the apparatus comprising:
   a plug portion comprising opposing engagement surfaces biased toward one another to anchor the medical device therebetween, the plug portion comprising a spring member adapted to bias the engagement surfaces, wherein the spring member includes a fixed end and a pair of opposing arms, each arm extending from the fixed end to a corresponding moveable end thereof;
   a ring member extending around a perimeter of the plug portion, wherein a slot extends from a slot opening formed through the ring member and into the plug portion, and wherein the ring member further comprises: opposing edges located on either side of the slot opening; and a mounting groove extending through the ring member on a side of the ring member opposite the slot opening, wherein each of the opposing edges overhangs the moveable end of the corresponding arm of the spring member; and
   a cap configured to cover the plug portion when fitted within the ring member, the cap including a first perimeter tab and a second perimeter tab opposite the first perimeter tab, wherein when the cap is fitted within the ring member to cover the plug portion, the first perimeter tab is located beneath the overhang of the opposing edges of the ring member, and the second perimeter tab is held within the mounting groove of the ring member.

* * * * *